(12) United States Patent
Imaizumi et al.

(10) Patent No.: US 7,385,083 B2
(45) Date of Patent: Jun. 10, 2008

(54) POTASSIUM CHANNEL OPENER

(75) Inventors: Yuji Imaizumi, Nagoya (JP); Tomohiko Ohwada, Tokyo (JP)

(73) Assignee: Tanabe Seiyaku Co., Ltd., Osaka (JP)

( * ) Notice: Subject to any disclaimer, the term of this patent is extended or adjusted under 35 U.S.C. 154(b) by 174 days.

(21) Appl. No.: 10/664,165

(22) Filed: Sep. 17, 2003

(65) Prior Publication Data

US 2004/0116482 A1  Jun. 17, 2004

Related U.S. Application Data

(63) Continuation-in-part of application No. PCT/JP02/04085, filed on Apr. 24, 2002.

(30) Foreign Application Priority Data

Apr. 25, 2001 (JP) ............................. 2001-127054
Nov. 2, 2001 (JP) ............................. 2001-337723

(51) Int. Cl.
- *C07C 65/01* (2006.01)
- *C07C 63/33* (2006.01)
- *C07C 62/12* (2006.01)
- *C07C 62/14* (2006.01)
- *C07C 62/22* (2006.01)

(52) U.S. Cl. ....................................... 562/466

(58) Field of Classification Search ................. 562/466
See application file for complete search history.

(56) References Cited

OTHER PUBLICATIONS

Singh et al, J. Chem. Soc. Perkins Trans. (1994), pp3349-3352.*
"Maxikdiol: A Novel Dihydroxyisoprimane as an Agonist of Maxi-K Channels", Sheo B. Singh, et al., *J. Chem. Soc. Perkin Trans.* 1, 1994, p. 3349-3352.
"Molecular Basis of Pimarane Compounds as Novel Activators of Large-Conductance $Ca^{2+}$-Activated $K^+$ Channel α-Subunit", Yuji Imaizumi et al.,Molecular Pharmacoology, vol. 62, p. 836-846 (2002).
"Dehydroabietic Acid Derivatives as a Novel Scaffold for Large-Conductance Calcium-Activated $K^+$ Channel Openers", Tomohiko Ohwada et al., Bioorg. Med. Chem. Lett., 13 p. 3971-3974 (2003).
English translation of the International Preliminary Examination Report in PCT/JP02/04085.
A. Ulubelen et al., "Cardioactive Terpenoids and a New Rearranged Diterpene from *Salvia syriace*" Planta Medica 66 (2000) 627-629.

* cited by examiner

*Primary Examiner*—Elvis O. Price
(74) *Attorney, Agent, or Firm*—Birch Stewart Kolasch & Birch

(57) ABSTRACT

A potassium channel opener comprising a compound (e.g., pimaric acid) represented by the formula [I]:

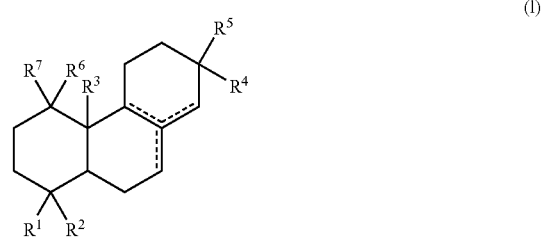

Figure 1:
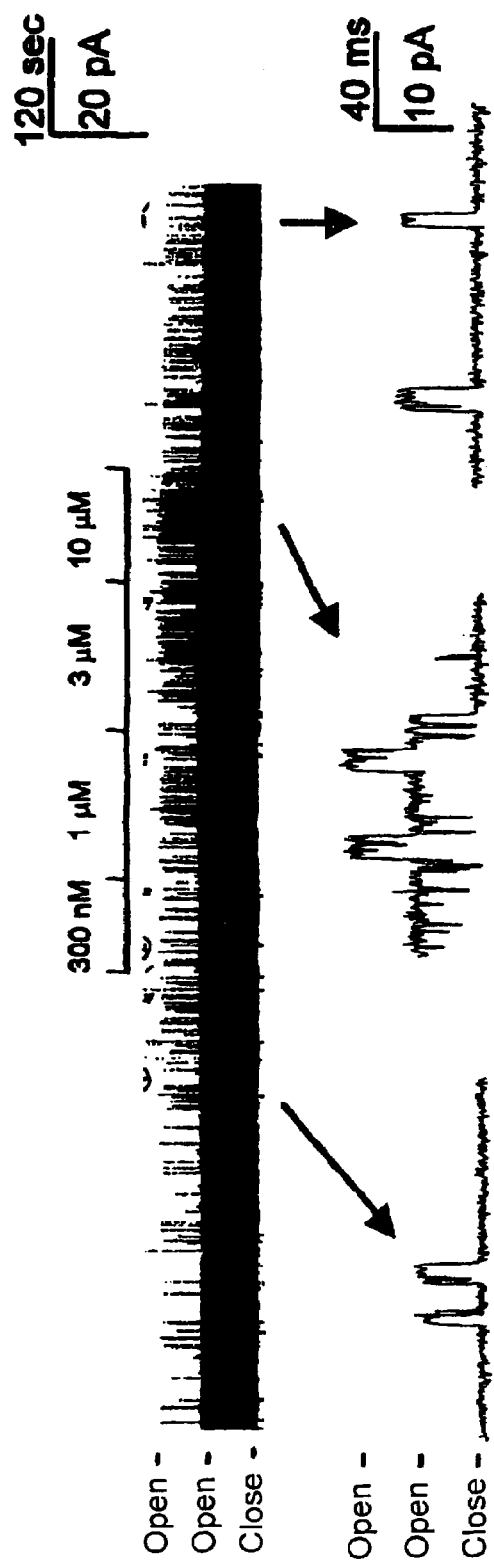

wherein $R^1$, $R^2$, $R^3$, $R^4$, $R^5$, $R^6$ and $R^7$ are each independently hydrogen, alkyl, alkenyl, halogen, hydroxy, halogenated alkyl, hydroxyalkyl, aminoalkyl, alkoxy, aryl, heteroaryl, acyl, carboxyl, alkoxycarbonyl, hydroxamate, sulfo, carbamoyl, sulfonamide, aldehyde, or nitrile; or $R^4$ and $R^5$ may be bonded to each other to form a ring; or $R^6$ and $R^7$ may be bonded to each other to form a ring; and all of three bonds represented by ═══ are single bonds, or one of the three bonds is double bond and the other bonds are single bonds, or a physiologically acceptable salt thereof as an effective ingredient.

5 Claims, 9 Drawing Sheets

POTASSIUM CHANNEL OPENER

This application is a continuation-in-part of PCT/JP02/04085, filed Apr. 24, 2002, and claims priority to Japanese Patent Application No. 2001-127054, filed Apr. 25, 2001 and Application No. 2001-337723, filed Nov. 2, 2001.

BACKGROUND OF THE INVENTION

1. Field of the Invention

The present invention relates to a potassium channel opener.

2. Background Art

Calcium-activated potassium channel (alternatively referred to as "BK channel") is present on cell membranes and is a protein which makes potassium ions permeate selectively. This channel protein has a calcium binding domain in an amino acid sequence facing intracellularly, and has a property of enhancing channel activity by binding of calcium. This means, the increase of intracellular calcium concentration leads to a higher chance of opening of the calcium-activated potassium channel (opening probability), thereby leading to an increase in permeability of cell membrane for potassium. There have been known three kinds of calcium-activated potassium channels, among which large conductance calcium-activated potassium channels are present in smooth muscles which are constituents of various kinds of organs, including blood vessel, bladder, bronchial tube, gastrointestinal tract, etc., and central or peripheral neuronal cells, however, they are not expressed in cardiac muscles.

Membrane potential is dependent on a balance of permeabilities of cell membrane for ions such as sodium, potassium, chloride, calcium, etc. When the potassium channel opening is selectively increased, potassium permeability becomes dominant, and cell is hyperpolarized. Therefore, opening of the calcium-activated potassium channels, for example, hyperpolarizes smooth muscle cells, lowers activities of voltage-dependent calcium channels, and inhibits influx of calcium from extracellular fluid. As a result, intracellular concentration of calcium decreases, leading to a relaxation of a smooth muscle. Accordingly, the opening of the calcium-activated potassium channels will make smooth muscle tissues relaxed, which are constantly under contraction (hypertension) in pathological states such as essential hypertension, tonic bladder, airway hyperresponsiveness, etc.

It also exhibits an inhibitory effect on hyperactivity, through hyperpolarization, in neuronal cells whose calcium concentration is increased due to hyperaction (hyperexcitement) caused by a strong stimulus. On the contrary, an administration of a BK channel blocker into central nervous system leads to convulsion in mice. As stated above, since pathological states due to a change in activity of potassium channels including calcium-activated potassium channels have recently become apparent, potential of treatment by potassium channel openers has been increased. Among them, a calcium-activated potassium channel opener is one of those that have been drawing most attention (Shieh, C. C., et al., Pharmacol. Rev., 52, pp.557–593, 2000).

As a substance having effect of activating calcium-activated potassium channels, there have been known maxikdiol (Singh, S., et al., J. Chem. Soc. Perkin. Trans. I, pp.3349-3352, 1994), dehydrosoyasaponin-I (MacManus, O. B., et al., Biocheminstry, 32, pp.6128–6133, 1993) and L-735,334 (Lee, S. H., et al., J. Nat. Prod., 58, pp.1822–1828, 1995), which are isolated from natural products, and as synthetic compounds, NS-1619 and its related compounds developed by NeuroSearch of Denmark, and Bristol-Myers Squibb of the United States (Olsen, S. P., et al., European patent publication No. 0477819A2, Olsen, S. P., et al., Euro. J. Pharmacol., 251, pp.53–59, 1994), and the like.

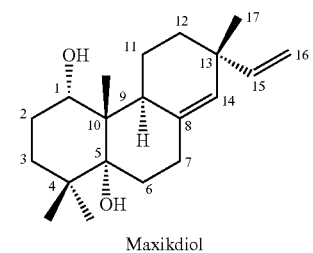

Maxikdiol

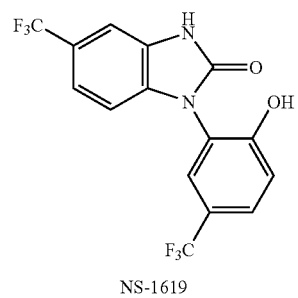

NS-1619

However, dehydrosoyasaponin-I and L-735,334 have relatively high molecular weights, and drawbacks in terms of their functional mechanism. NS-1619 related compounds have low activities, and have a problem that their actions are not specific. Further, although maxikdiol has an excellent activity, it is extremely difficult to obtain, since it is a natural product. Therefore, there have been needs for development of an agent having a BK channel opening activity equivalent to or higher than that of maxikdiol, and having a high specificity of the activity.

SUMMARY OF THE INVENTION

The object of the present invention is to provide a potassium channel opener, preferably a calcium-activated potassium channel opener. More specifically, the object of the present invention is to provide a potassium channel opener, preferably a calcium-activated potassium channel opener, which has BK channel opening activity which is equivalent to or higher than that of maxikdiol, and has high specificity of the activity. The present inventors have carried out intensive studies to solve the above stated problems, and as a result, they have found that pimaric acid and its derivatives have extremely excellent potassium channel opening actions, and that these actions are specific. The present invention has been completed based on the above findings.

Accordingly, the present invention provides a potassium channel opener comprising a compound represented by the following formula (I):

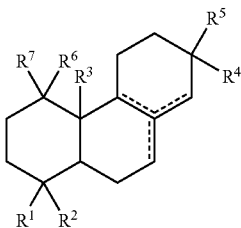

wherein $R^1$, $R^2$, $R^3$, $R^4$, $R^5$, $R^6$ and $R^7$ are each independently hydrogen, alkyl, alkenyl, halogen, hydroxy, halogenated alkyl, hydroxyalkyl, aminoalkyl, alkoxy, aryl, heteroaryl, acyl, carboxyl, alkoxycarbonyl, hydroxamate (—C(O)NHOH), sulfo (—SO$_3$H), carbamoyl (—CONH$_2$), sulfonamide (—SO$_2$NH$_2$), aldehyde or nitrile; or $R^4$ and $R^5$ may be bonded to each other to form a ring; or $R^6$ and $R^7$ may be bonded to each other to form a ring; and all of three bonds represented by ----- are single bonds, or one of the three bonds is double bond and the other bonds are single bonds, or a physiologically acceptable salt thereof as an active ingredient.

As a preferred embodiment of the present invention, provided is the above mentioned potassium channel opener comprising as an effective ingredient a compound wherein $R^1$, $R^3$, $R^4$ and $R^5$ are alkyl or alkenyl, $R^6$ and $R^7$ are hydrogen, and $R^2$ is carboxyl, or a physiologically acceptable salt thereof. As a more preferred embodiment, provided is the above mentioned potassium channel opener comprising as an effective ingredient a substance selected from the group consisting of the following compounds: (1) a compound wherein $R^1$ is alkyl, $R^2$ is carboxyl, $R^3$ is alkyl, $R^4$ is alkenyl, $R^5$ is alkyl, and $R^6$ and $R^7$ are hydrogen (2) a compound wherein $R^1$ is alkyl, $R^2$ is carboxyl, $R^3$ is alkyl, $R^4$ is alkyl, $R^5$ is alkenyl, and $R^6$ and $R^7$ are hydrogen, and (3) a compound wherein $R^1$ is alkyl, $R^2$ is carboxyl, $R^3$ is alkyl, $R^4$ is alkyl, $R^5$ is alkyl, and $R^6$ and $R^7$ are hydrogen, and a physiologically acceptable salt thereof. And as a further preferred embodiment, provided is the above mentioned potassium channel opener comprising as an effective ingredient a substance selected from the group consisting of pimaric acid, dihydropimaric acid, dihydroisopimarinol, sandaracopimaric acid, isopimaric acid, and dihydroisopimaric acid, and a physiologically acceptable salt thereof.

Further, the present invention provides a potassium channel opener comprising a compound represented by the following formula (II):

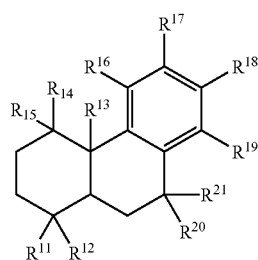

wherein $R^{11}$, $R^{12}$, $R^{13}$, $R^{14}$, $R^{15}$, $R^{16}$, $R^{17}$, $R^{18}$, $R^{19}$, $R^{20}$ and $R^{21}$ are each independently hydrogen, alkyl, alkenyl, halogen, hydroxy, halogenated alkyl, hydroxyalkyl, aminoalkyl, alkoxy, aryl, heteroaryl, acyl, carboxyl, alkoxycarbonyl, hydroxamate, sulfo, carbamoyl, sulfonamide, aldehyde or nitrile; or $R^{20}$ and $R^{21}$ may be bonded to each other to form oxo, or a physiologically acceptable salt thereof as an active ingredient.

As a preferred embodiment of the present invention, provided is the above mentioned potassium channel opener comprising as an effective ingredient a compound wherein $R^{11}$, $R^{13}$ and $R^{18}$ are alkyls, $R^{12}$ is carboxyl, and $R^{14}$, $R^{15}$ and $R^{16}$ are hydrogen, or a physiologically acceptable salt thereof. As a more preferred embodiment, provided is the above mentioned potassium channel opener comprising as an effective ingredient a compound wherein $R^{11}$, $R^{13}$ and $R^{18}$ are alkyls, $R^{12}$ is carboxyl, $R^{14}$, $R^{15}$, $R^{16}$, $R^{20}$ and $R^{21}$ are hydrogen, and $R^{17}$ and $R^{19}$ are halogen or a physiologically acceptable salt thereof.

The above mentioned potassium channel opener provided by the present invention is preferably a calcium-activated potassium channel opener, and may be used for prevention and/or treatment of, for example, essential hypertension, tonic bladder, airway hyperresponsiveness, or ischemic central nervous system disorder.

From another point of view, the present invention provides a use of the compound represented by the above formula (I) or formula (II) or physiologically acceptable salt thereof for preparation of the above potassium channel opener; a method for prevention and/or treatment of essential hypertension, tonic bladder, airway hyperresponsiveness, or ischemic central nervous system disorder, comprising a step of administering the compound of the above formula (I) or the formula (II) or a physiologically acceptable salt thereof, in an effective dose for prevention and/or a treatment to a mammal including a human; and a method of opening a potassium channel, preferably a calcium-activated potassium channel, comprising a step of administrating an effective dose of the compound of the above formula (I) or the formula (II) or a physiologically acceptable salt thereof to a mammal including a human.

Further, there are provided a method for relaxing a smooth muscle in a mammal including a human, comprising a step of administering an effective dose of the above compound of the formula (I) or the formula (II) or a physiologically acceptable salt thereof to a mammal including a human; a method of protecting a central nervous system in a mammal including a human, comprising a step of administering an effective dose of the compound of the above formula (I) or the formula (II) or a physiologically acceptable salt thereof to a mammal including a human; a method of hyperpolarizing a smooth muscle cell in a mammal including a human, comprising a step of administering an effective dose of the compound of the above formula (I) or the formula (II) or a physiologically acceptable salt thereof to a mammal including a human; and a method of hyperpolarizing a neuron of a central nervous system in a mammal including a human, comprising a step of administering an effective dose of the compound of the above formula (I) or the formula (II) or a physiologically acceptable salt thereof to a mammal including a human.

BRIEF DESCRIPTIONS OF THE DRAWINGS

FIG. 1 shows results of activation of BKα channels upon administration of pimaric acid. The upper section and the lower section show, respectively, a trace with a fast lapse of time and a trace with a slow lapse of time.

Figure 2:
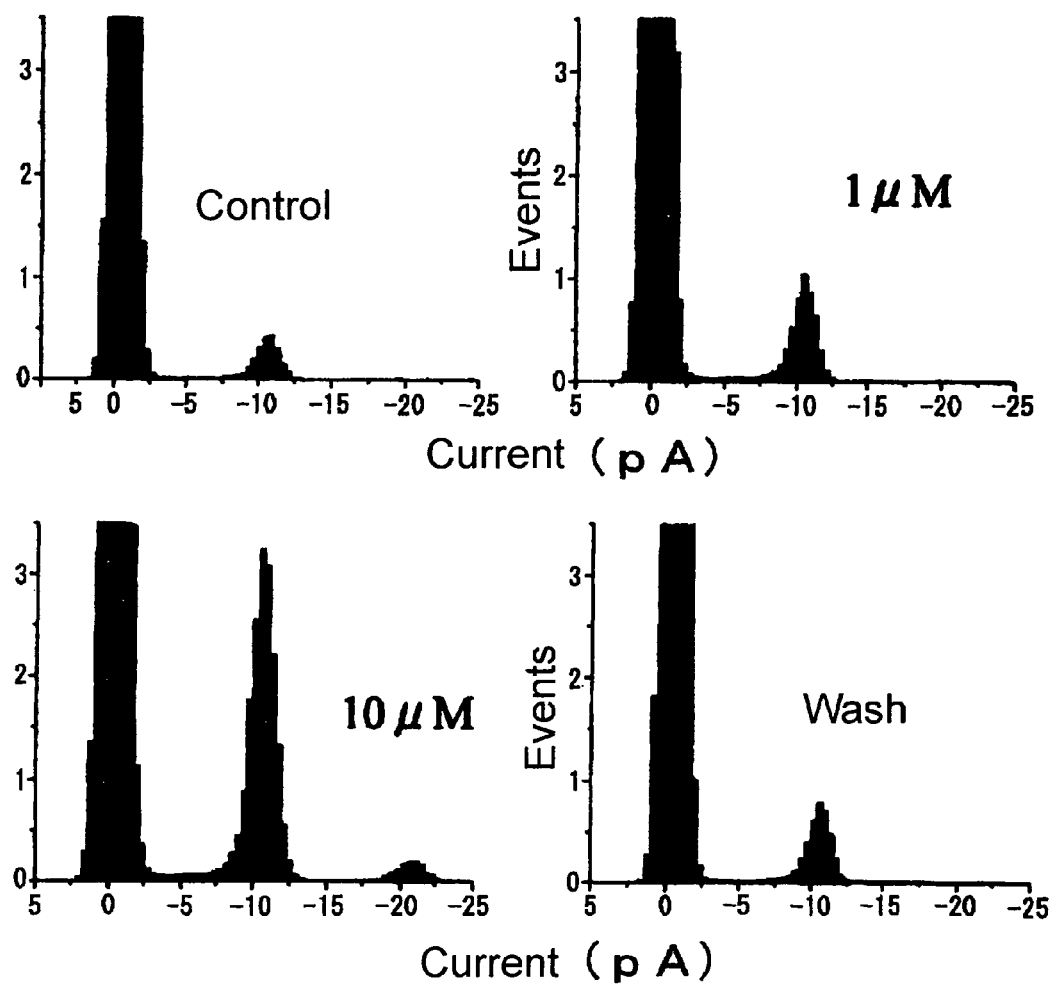

FIG. 2 shows histograms of single BKα channel currents (horizontal axis) before application of pimaric acid, after application of 1 μM, after application of 10 μM, and after washout, and their frequencies of events per unit time (vertical axis). In the figure, CONTROL means results of reference, 1 μM means results of after application of 1 μM, 10 μM means results of after application of 10 μM, and WASH OUT means results of after washout.

Figure 3:
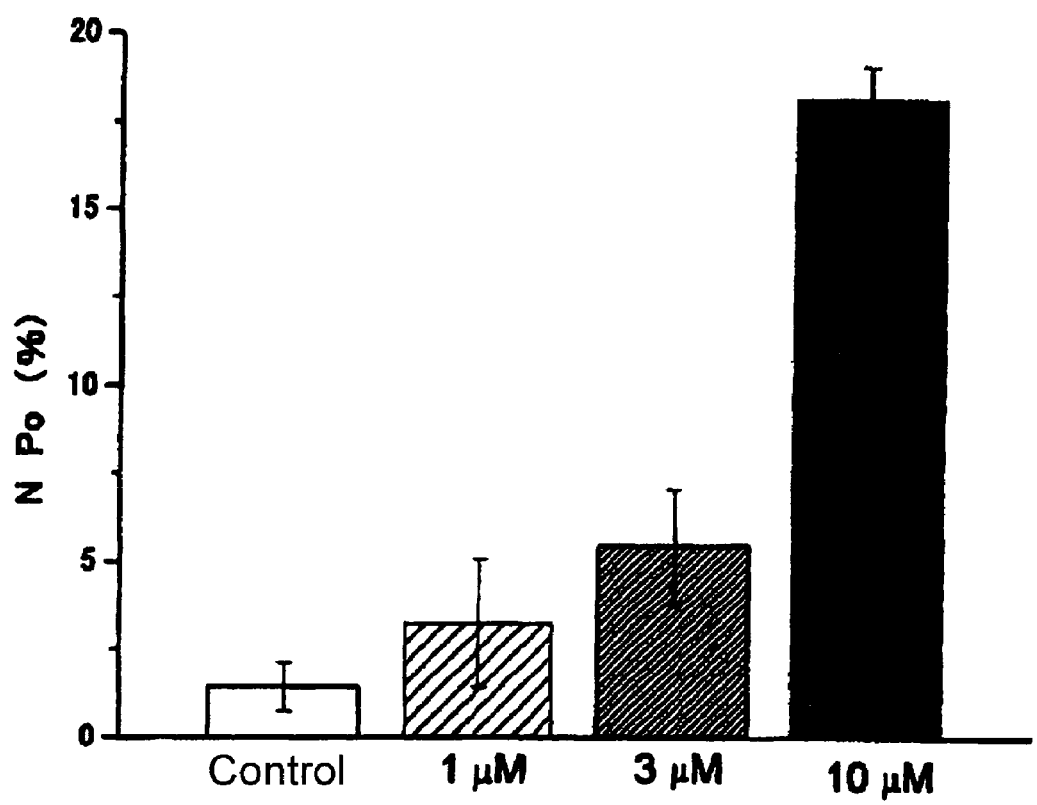

FIG. 3 shows a relation between a concentration of pimaric acid and an effect of BKα channel activation. The vertical axis shows an opening probability (NPo), and the horizontal axis shows a concentration of pimaric acid.

FIG. 4 shows a result of BKαβ1 channel activation by administration of dichloridehydroabietic acid as a representative compound of the compounds represented by the formula (II) (whole-cell current recording). In the figure, A shows a periodical change accompanied by drug administration, B shows original traces of currents at respective points shown in the figure A, and C shows concentration-effect relations in terms of BK (α+β1) current enhancing effect, for 3 kinds of test compounds. In the figure C, ○ shows results of dichlorodehydroabietic acid (2Cl·DhA), □ shows results of abietic acid (AbA), and ▲ shows results of pimaric acid (PiA).

FIG. 5 shows a result of BKαβ1 channel activation by administration of dichloridehydroabietic acid as a representative compound of the compounds represented by the formula (II) (single-channel current recording). In the figure, A shows results of observing changes in channel opening probability when the holding potential was maintained at +40 mV, B shows histograms of channel opening and closing events, obtained from original traces, and C shows a relation between concentration and effect.

DESCRIPTION OF THE PREFERRED EMBODIMENTS

The terms used in the present specification have the following meanings.

When "alkyl" is referred to, it means any form of straight, branched, cyclic, and a combination thereof. For example, $C_1$–$C_{12}$ alkyl, preferably $C_1$–$C_8$ alkyl, more preferably $C_1$–$C_6$ alkyl, and particularly preferably $C_1$–$C_4$ alkyl may be used. The alkyl moiety in the substituents having an alkyl moiety referred to in the present specification (e.g., alkenyl, halogenated alkyl, alkoxy, hydroxyalkyl, etc.) has the same meaning.

Positions and number of the double bonds contained in alkenyl are not particularly limited, and the number of the double bonds is preferably 1 to 3, more preferably 1 or 2, and particularly preferably 1. As the alkenyl, preferred is allyl or vinyl and particularly preferred is vinyl. When geometric isomers arise based on the double bond, configuration of the double bond may either of Z or E.

"Halogen atom" (or "halogen") means any of fluorine atom, chlorine atom, bromine atom and iodine atom. Kind, number and substituting position of the halogen atom appearing on "halogenated alkyl" are not particularly limited, and the halogen atom may be any of fluorine atom, chlorine atom, bromine atom or iodine atom, and preferred is fluorine atom or chlorine atom. As the halogenated alkyl, for example, trihalogenated methyl is preferred and trifluoromethyl or trichloromethyl is particularly preferred.

Number and substituting position of hydroxy appearing on "hydroxyalkyl" are not particularly limited, and the number is preferably 1 to around 4, more preferably 1 or 2, and particularly preferably 1. As the hydroxyalkyl, for example, hydroxymethyl is preferred. Number and substituting position of amino appearing on "aminoalkyl" are not particularly limited, and the number is preferably 1 to around 4, more preferably 1 or 2, and particularly preferably 1. As the aminoalkyl, aminomethyl is preferred.

As the "aryl", it may be either of monocyclic or condensed aryl. For example, phenyl or naphthyl may be used.

"Heteroaryl" means, for example, heteroaryl containing 1 or 2 or more hetero atom(s) selected from the group of nitrogen, oxygen and sulfur as a ring constituting atom. As such examples, there may be mentioned pyridyl, furyl, thienyl or pyrrolyl. "Acyl" means either of arylcarbonyl such as benzoyl, or alkanoyl such as acetyl.

Alkyl, alkenyl, halogenated alkyl, hydroxyalkyl, alkoxy, aryl, heteroaryl, acyl, alkoxycarbonyl, hydroxamate, carbamoyl, or sulfonamide represented by $R^1$, $R^2$, $R^3$, $R^4$, $R^5$, $R^6$ and $R^7$, and $R^{11}$, $R^{12}$, $R^{13}$, $R^{14}$, $R^{15}$, $R^{16}$, $R^{17}$, $R^{18}$, $R^{19}$, $R^{20}$ and $R^{21}$, may further have one or two or more substituent(s). Kind, substituting position and number of the substituents are not particularly limited, and when it has two or more substituents, they may be the same or different. For example, as a case where aryl has a substitutent, there may be mentioned fluorophenyl, hydroxyphenyl, etc. and as a case where acyl has a substituent, there may be mentioned chlorobenzoyl, trifluoroacetyl, etc., however, the examples of the substituents are not limited to these.

"Ring" formed by bonding $R^4$ and $R^5$, or by bonding $R^6$ and $R^7$ is exemplified by $C_3$–$C_7$ cycloalkane ring such as cyclopropane, cyclobutane, cyclopentane, cyclohexane and cycloheptane.

In the compounds represented by the above formula (I) or the formula (II), as shown in the present specification, when the stereochemistry of the compound is not shown, it means the compound may be any steroisomer, and pure form of any stereoisomer, any mixture of stereoisomers, racemates, a mixture of diastereoisomers and the like are included in the scope of the present invention.

As preferred examples of the compound represented by the formula (I), there may be mentioned the following compound groups A1 to A4. Configurations in the following formulae A1 to A4 show the absolute configurations.

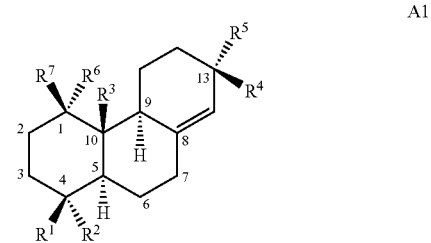

A1

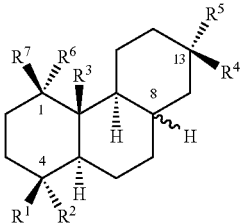

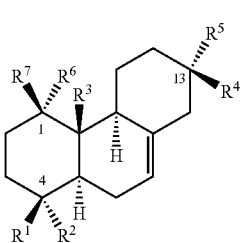

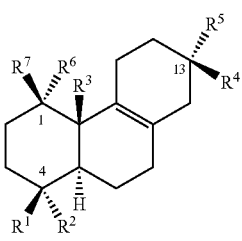

Preferably, $R^1$, $R^3$, $R^4$, and $R^5$ are each independently alkyl or alkenyl. Preferred is a case where $R^1$ is alkyl, $R^3$ is alkyl, $R^4$ is alkenyl and $R^5$ is alkyl, or a case where $R^1$ is alkyl, $R^3$ is alkyl, $R^4$ is alkyl and $R^5$ is alkenyl. More preferred is a case where $R^1$ is methyl, $R^3$ is methyl, $R^4$ is vinyl or ethyl and $R^5$ is methyl or a case where $R^1$ is methyl, $R^3$ is methyl, $R^4$ is methyl and $R^5$ is vinyl or ethyl.

$R^2$ is preferably carboxyl, hydroxamate, sulfo, carbamoyl, sulfonamide, aldehyde, or nitrile, and more preferably carboxyl. $R^6$ and $R^7$ are both preferably hydrogen atoms. Particularly preferable compounds are the following compounds.

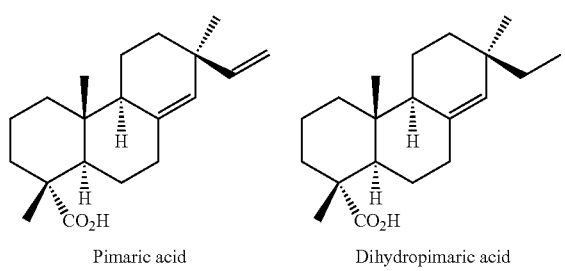

Pimaric acid  Dihydropimaric acid

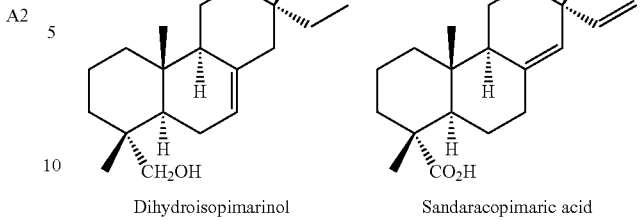

Dihydroisopimarinol  Sandaracopimaric acid

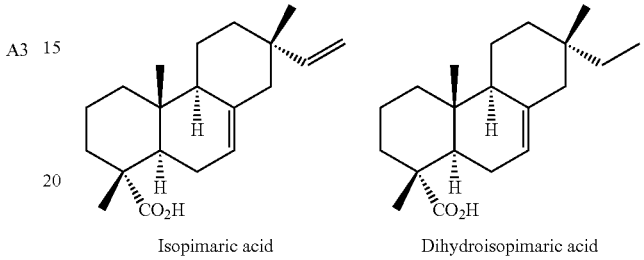

Isopimaric acid  Dihydroisopimaric acid

Among the particularly preferable compounds as shown above, pimaric acid is a known compound as a resin acid component. Further, sandaracopimaric acid, isopimaric acid, and dihydroisopimaric acid are commercially available. The compounds represented by the formula (I) may be prepared by, for example, using the above mentioned pimaric acid, dihydropimaric acid, sandaracopimaric acid, isopimaric acid, or dihydroisopimaric acid as a starting material, carrying out conversion of functional groups, which are conventionally known to the person skilled in the art. For example, dihydropimaric acid in which $R^4$ is ethyl can be prepared by reducing vinyl existing as $R^4$ in pimaric acid by a conventionally means, and a compound in which $R^2$ is alkoxycabonyl can be prepared by esterifying carboxyl existing as $R^2$ in pimaric acid.

Further, in the compounds represented by the formula (II), preferred stereochemistry is as shown below (configurations in the formulae show absolute configurations), and preferred is a case where $R^{11}$, $R^{13}$ and $R^{18}$ are alkyls, $R^{12}$ is carboxyl, and $R^{14}$, $R^{15}$ and $R^{16}$ are hydrogen, and more preferred is a case where $R^1$, $R^{13}$ and $R^{18}$ are alkyls, $R^{12}$ is carboxyl, $R^{14}$, $R^{15}$, $R^{16}$, $R^{20}$ and $R^{21}$ are hydrogen, and $R^{17}$ and $R^{19}$ are halogen. As the alkyl represented by $R^{11}$ and $R^{13}$, methyl is preferred, and as the alkyl represented by $R^{18}$, ethyl, n-propyl, isopropyl, n-butyl, sec-butyl, tert-butyl, etc. are preferred. As the alkyl represented by $R^{18}$, particularly preferred is isopropyl. As the halogen represented by $R^{17}$ and $R^{19}$, preferred is chlorine.

Further, in the compounds represented by the formula (II), also preferred is a compound in which $R^{20}$ is hydroxy, and $R^{21}$ is a hydrogen atom, and a compound in which $R^{20}$ and R are taken together to form oxo. For example, preferred is a compound in which $R^{11}$, $R^{13}$ and $R^{18}$ are alkyls, $R^{12}$ is carboxyl, $R^{14}$, $R^{15}$ and $R^{16}$ are hydrogen, $R^{17}$ and $R^{19}$ are halogen or hydrogen, $R^{20}$ is hydroxy, and $R^{21}$ is hydrogen, and a compound in which $R^{11}$, $R^{13}$ and $R^{18}$ are alkyls, $R^{12}$ is carboxyl, $R^{14}$, $R^{15}$ and $R^{16}$ are hydrogen, $R^{17}$ and $R^{19}$ are halogen or hydrogen, and $R^{20}$ and $R^{21}$ are taken together to form oxo. More specifically, as preferred compounds of the formula (II), the following compounds may be exemplified, among which the compound represented by (1) is particularly preferred. All of the following compounds of (1) to (3) are commercially available.

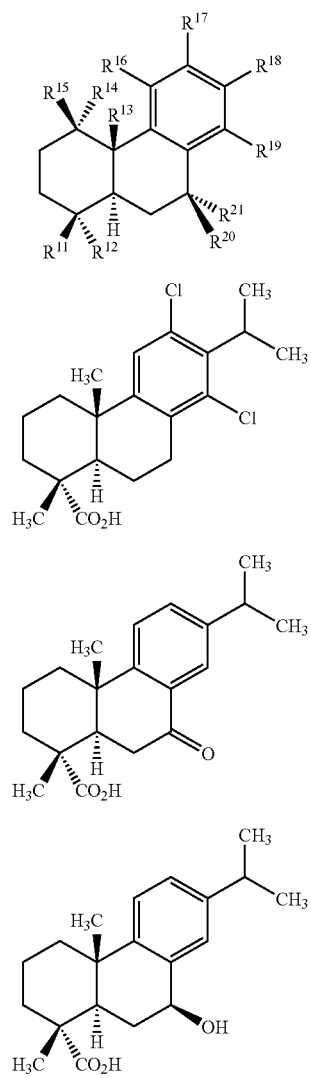

As an active ingredient of the potassium channel opener of the present invention, besides the compounds represented by the above formula (I) or the formula (II), physiologically acceptable salts thereof depending on the kinds of substituents may be used. Kinds of the salts are not particularly limited as long as they are physiologically acceptable, and the salts may be either of acid addition salts or base addition salts. As the acid addition salt, there may be mentioned, for example, a mineral acid salt such as chloride, sulfate, nitrate, etc. and an organic salt such as p-toluenesulfonate, methanesulfonate, oxalate, maleate, tartrate, etc. And as the base addition salt, there may be mentioned a metal salt such as a sodium salt, a potassium salt, a calcium salt, etc. and an organic amine salt such as an ammonium salt, a triethylamine salt, an ethylamine salt, etc. Also, a salt with an amino acid such as glycine may be used.

As an active ingredient of the potassium channel opener of the present invention, besides the compound in a free form and the physiologically acceptable salt thereof, any hydrates or solvates thereof may be used. There is no particular limitation to kinds of solvents to form the solvates, and for example, acetone, ethanol, tetrahydrofuran, etc. may be mentioned. Further, the compound of the above formula (I) or the formula (II) may further have one or more asymmetric carbons besides the asymmetric carbons contained in the above formulae, depending on kinds of substitutents. Therefore, stereoisomers such as optically active isomers or diastereoisomers based on the asymmetric carbons may exist, and pure form of stereoisomers, any mixture of stereoisomers, racemates, etc. may be used as an active ingredient of the potassium channel opener of the present invention.

Although it is not our intension to be bound by any specific theory, the potassium channel opener of the present invention acts on calcium-activated potassium channel proteins being present in smooth muscle which are constituents of various kinds of organs, including blood vessel, bladder, bronchial tube, gastrointestinal tract, etc., and central or peripheral nervous system, and increases chance of opening of the respective calcium-activated potassium channels per unit time (opening probability), thereby increasing potassium permeability of cell membrane. This leads to hyperpolarization of smooth muscle cells and lowers activities of voltage-dependent potassium channels. And by inhibiting calcium influx from extracellular fluid, smooth muscle is relaxed and neuronal cells are protected from damages caused by calcium overload.

Therefore, the potassium channel opener of the present invention can relax smooth muscle tissues, which are constantly under contraction (hypertension) in pathological states such as hypertension including essential hypertension, tonic bladder, disturbances of peripheral circulation, airway hyperresponsiveness, sensory neuron hypersensitivity, central spasm, etc., and is useful as a medicament for preventing and/or treating these diseases. Further, it is useful as a medicament for protecting neuronal cells of central or peripheral nervous system, particularly, neuronal cells of central nervous system. In spite of the above, an object of application of the potassium channel of the present invention is not limited to the above mentioned particular diseases, and it is applicable for various diseases which can be prevented and/or treated by relaxing smooth muscle, and various diseases which can be prevented and/or treated by protecting neuronal cells.

The potassium channel opener of the present invention may comprise one kind or two or more of the substances selected from the group consisting of the compounds of the above formula (I) and the formula (II) and physiologically acceptable salts thereof, and hydrates and solvates thereof.

As a medicament of the present invention, the above substances may be administered as they are, and preferably, they may be administered as a pharmaceutical composition for oral or parenteral administration, which can be prepared according to conventionally known methods for person skilled in the art. As the pharmaceutical composition suitable for oral administrations, tablets, capsules, powders, fine granules, granules, liquid, or syrup, etc. may be exemplified, and as the pharmaceutical composition suitable for parenteral administration, injections, infusions, suppositories, inhalants, eye drops, nasal drops, ear drops, ointment, cream, percutaneous absorbents, permucosal absorbents, adhesive plaster, etc. may be exemplified.

One kind or two or more of formulation additives may be added to prepare the above pharmaceutical compositions. As the formulation additives, excipients, disintegrators or disintegrating aids, binders, lubricants, coating agents, pigments, diluents, bases, solvents or solubilizing aids, isotonic agents, pH buffers, stabilizer, propellants, adhesives, etc. may be exemplified. They may be optionally selected depending on the forms of the pharmaceutical compositions.

The dose of the potassium channel opener of the present invention is not particularly limited, and it is optionally selected depending on kinds of actions and strength of the actions, and it may be optionally adjusted depending on various factors to be generally considered, including weights or ages of the patients, kinds and conditions of diseases, and its administration route. Generally, in case of oral administration, it can be used in a range of 0.01 to 1,000 mg, per an adult per day.

EXAMPLES

In the following, the present invention is explained in more detail by referring to Examples, however, the present invention is not limited by these Examples. Pimaric acid used in Examples were purchased from ICN, Inc. of the United States.

Example 1

(A) Experimental System

Calcium-activated potassium channel (hereinafter abbreviated as "BK channel" in Examples) functions with two kinds of proteins α (BKα) and β (BKβ) subunits being arranged in tetramers. BKα consists a main part of a channel and BKβ is an activity regulating factor. In order to selectively detect BK channel opening effect, BK channels were artificially expressed on cultured cells which do not originally have the BK channels (cultured cells derived from human embryonic kidney, HEK293 cells) by gene transfection, to constitute an experimental system. In accordance with a method of Ahring, et al. (Ahring P. K., et al., FEBS Lett., 415, pp.67–70, 1997), cDNAs of BKα and BKβ1 genes derived from rat uterus smooth muscle (GenBank accession numbers; U55995 and AF020712) were introduced into HEK293 cells by using calcium phosphate coprecipitation transfection techniques, to constantly overexpress BKα or BKαβ.

(B) Methods and Results (a) Single Channel Current Recording by Inside-Out Patch clamp technique By using Inside-out patch clamp technique, fragments of cell membrane containing the channels were isolated, and by artificially controlling an environment of inside of the cell membrane, opening or closing of a single channel can be directly observed. This is a fully established method not only for functional analysis of the channel, but also for testing quantitative effects of the channel agonists (Hamil, O. P., et al., Pflgers Archiv., 391, pp.85–100, 1981). BKα and BKαβ expressed on HEK293 cells that were used in the present measurement, both showed single channel conductance of 230–240 pS when solutions inside and outside of the patch membrane contains 140 mM K, and they were confirmed to have properties which correspond well to those in the prior literatures.

Under this condition, action and effect of pimaric acid for BKα was measured. The upper section of FIG. 1 shows BKα single channel recording when the patch membrane potential is kept so that inside of the cell is +40 mV relative to the outside of the cell, and intercellular Ca concentration is 0.1 µM (the upper section: upward rectangles show currents due to channel openings). When pimaric acid was added to the solution of the inner side of the cell membrane, at a concentration of 10 µM or less, channel activity is significantly increased (the middle section), and the action disappeared when pimaric acid was washed away.

FIG. 2 shows results of carrying out such current recordings for 30 seconds, as histograms. In Current Amplitude, 0 pA means a closing state. Addition of pimaric acid at a concentration of 1 µM or 10 µM increased time of an opening state, and particularly, in case of 10 µM it was shown that there were cases where two channels simultaneously opened. In FIG. 3, a relation between a concentration of pimaric acid and an effect of BK channel activation is shown under this condition. By addition of pimaric acid at concentration of 3 µM or more, a significant increase in channel opening probability was confirmed. Further, when Ca concentration of the inner side of the cell membrane is 0.3 µM, and the patch membrane potential is +40 mV, the opening probability at 1 µM increased by three times.

(b) Membrane Current Recording by Whole Cell Voltage-Clamp Technique

Membrane current of the whole cell by opening of BKα channels was recorded by Whole cell voltage-clamp technique. This technique is frequently employed to analyze the functions shown by the ion channels expressed in numbers on a cell membrane as a whole, and is a well established technique (Hamil, O. P. the above mentioned reference). When this technique was applied to a single HEK293 cell on which BKα channels were expressed, 1 µM of pimaric acid added to extracellular fluid increased BKα current by about 50% at +60 mV, showing a significant channel opening action. Since the action of pimaric acid was completely inhibited by addition of 1 mM tetraethylammonium, which is a BK channel inhibitor, it was confirmed that the action of pimaric acid was an opening of BK channel.

From the above results, it was shown that Pimaric acid acts on BKα, exhibiting BK channel opening effect and that the action was exhibited by administration of Pimaric acid to extracellular fluid, and it was removed immediately by washout, and the effect was at least three times or more as much as the effect of maxikdiol described in the reference. It is thought to have an effect of 10 times or more as much as that of NS-1619, which is a known compound which is known to have a BK channel opening effect. From these results, it can be concluded that Pimaric acid is extremely useful as a BK channel opener.

Example 2

As a compound represented by the formula (II), the above shown compound (1) (dichlorodehydroabietic acid) was used to analyze BK channel opening effect.

(1) Material and Method (a) Whole Cell Current Recording

According to the whole-cell patch clamp technique, whole-cell currents were recorded on HEK293 cell, in which rat BKα+β1 subunits were constantly expressed. All the experiments were carried out at 22–24° C.

Solution:

Pipette solution (mM) 140 KCl, 4 $MgCl_2$, 5 ATP, 10 HEPES, 5 EGTA (the pCa was adjusted to 6.5 by adding a suitable amount of $CaCl_2$ to stabilize the pCa). The pH was adjusted to 7.2 with KOH.

Extracellular fluid (mM) 137 NaCl, 5.9 KCl, 2.2 $CaCl_2$, 1.2 $MgCl_2$, 14 Glucose, 10 HEPES. The pH was adjusted to 7.4 with NaOH.

(b) Single-channel Recording

According to the inside-out patch clamp technique, a single channel current was recorded on HEK293, in which rat BKα+ α1 subunits were constantly expressed. All the experiments were carried out at 22–24° C.

Solution:

Intracellular fluid (mM) 140 KCl, 1.2 $MgCl_2$, 14 Glucose, 5 EGTA (the pCa was adjusted to 7 by adding a suitable amount of $CaCl_2$ to stabilize the pCa). The pH was adjusted to 7.2 with NaOH.

Extracellular fluid (mM) 140 KCl, 4 $MgCl_2$, 5 ATP, 10 HEPES, 0.05 EGTA. The pH was adjusted to 7.2 with KOH.

Since the test compounds were highly aliphatic, and hard to dissolve in water, they were dissolved by DMSO and preserved as 30 mM stock solutions. On administration, final concentration in the DMSO solutions were made at most 0.03%. Incidentally, DMSO was confirmed not to have any influence on BK currents, when its concentration is 0.3% or less.

Figure 4A:
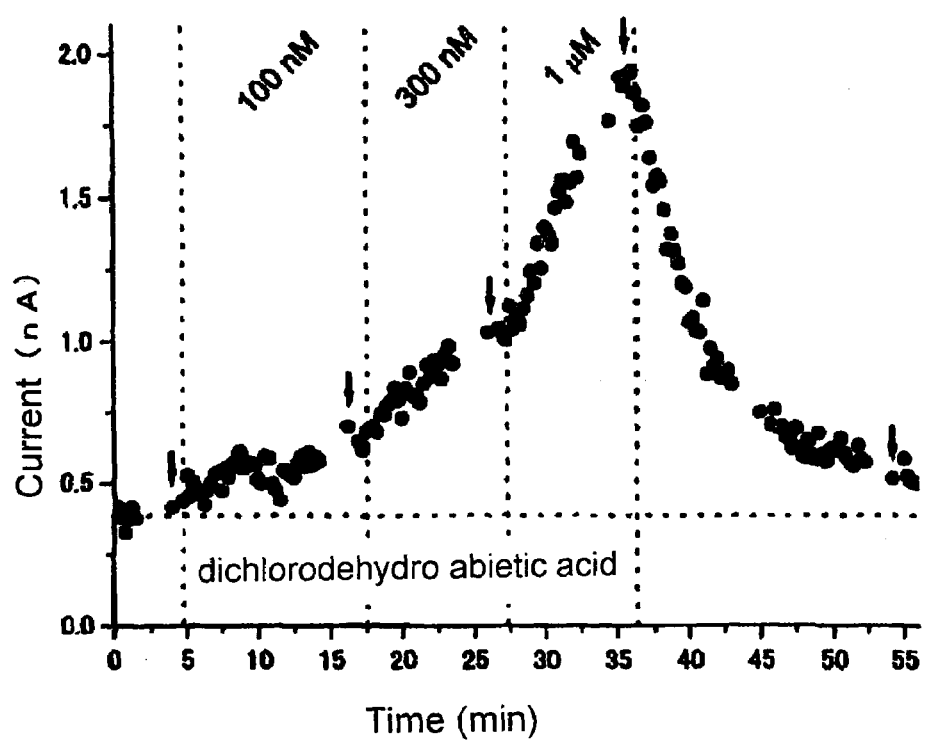
Figure 4B:
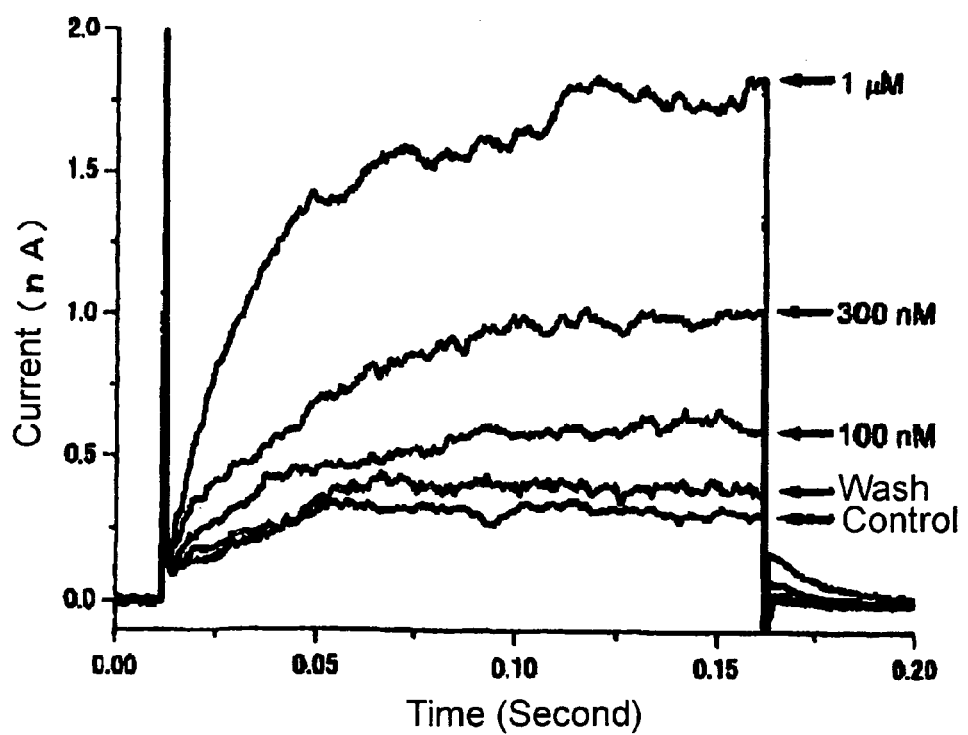
Figure 4C:
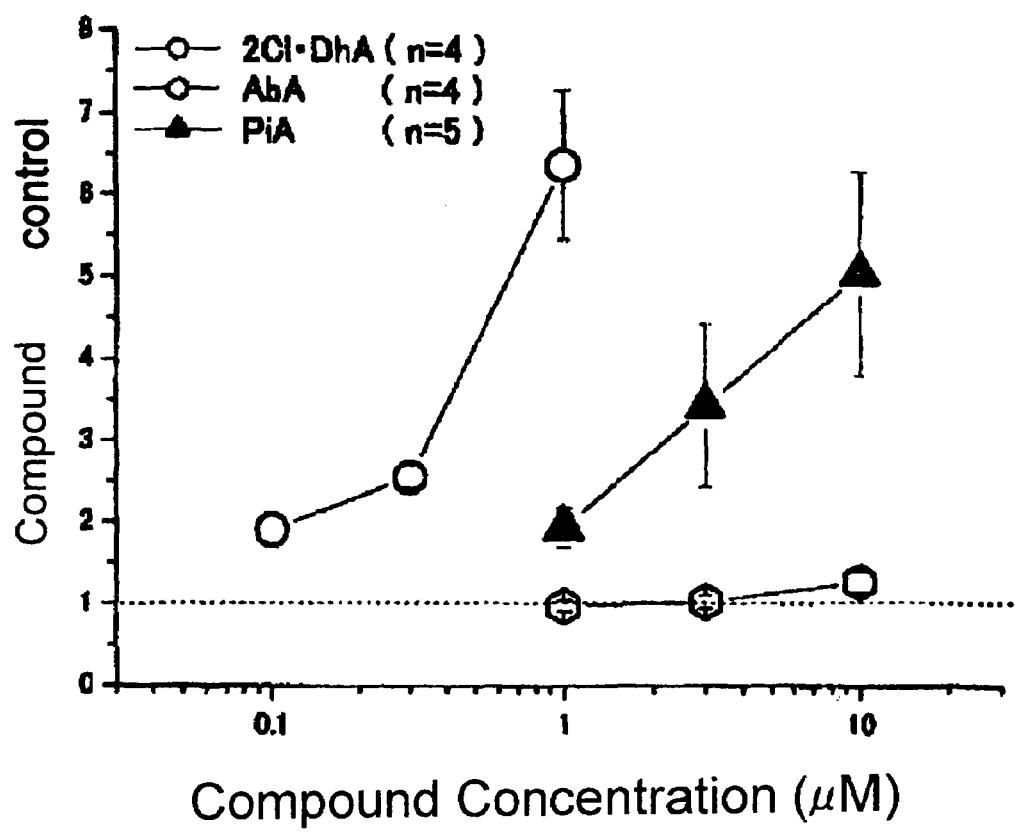

(2) Results The whole-cell currents were recorded with the cells in which BK(α+β1) channels were constantly expressed, by the whole-cell patch clamp technique. The $Ca^{2+}$ concentration in the intracellular fluid was fixed at pCa 6.5 with $Ca^{2+}$-EGTA buffer. The pulse depolarizing from the resting potential −60 mV to +10 mV, was added for 150 mseconds, and the elicited currents were observed. By the depolarizing stimulus, moderately activated outward currents were observed, which are characteristic of BK(α+β1) channel (control in FIG. 4B). After establishing the whole cell, the recording was started at a point where stable current measurements were obtained for 20 minutes. When 100 nM of the test compound was applied, the currents were enhanced in course of time, and as the concentration of the test compounds increases, the currents were observed to become larger correspondingly. After that, by washout, the current went back almost to the level prior to application of the test compounds (FIG. 4A). As a result of a statistical analysis based on the recordings of the 4 examples, the currents were activated by 1.90±0.21 times at concentration of 100 nM, 2.54±0.14 times at 300 nM, and 6.37±0.91 times at 1 μM, by this activating effect. As compared to the fact that pimaric acid activated the current by 1.92±0.24 times at 1 μM, it was shown to have a clearly stronger effect (FIG. 4C).

Figure 5A:
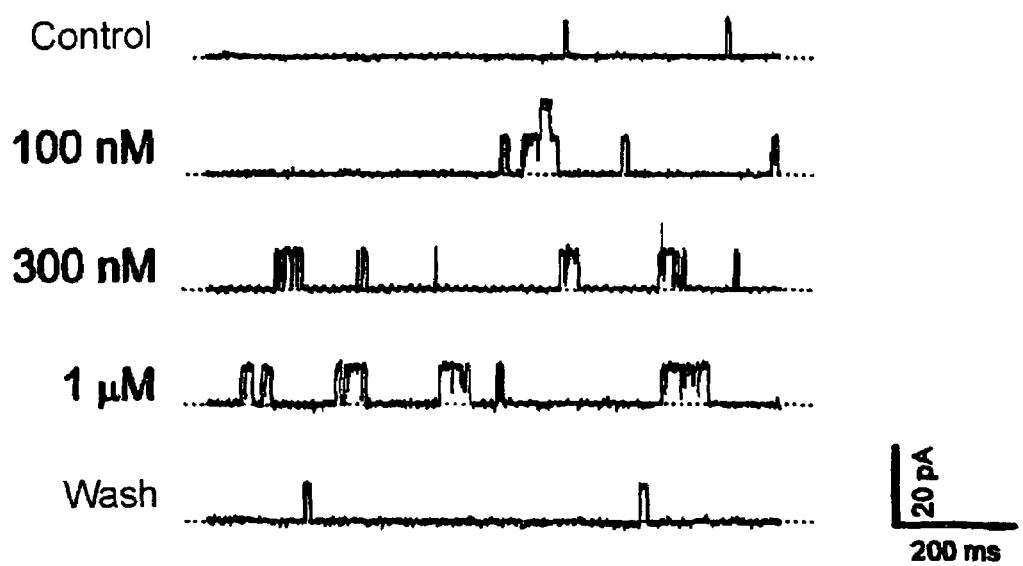
Figure 5B:
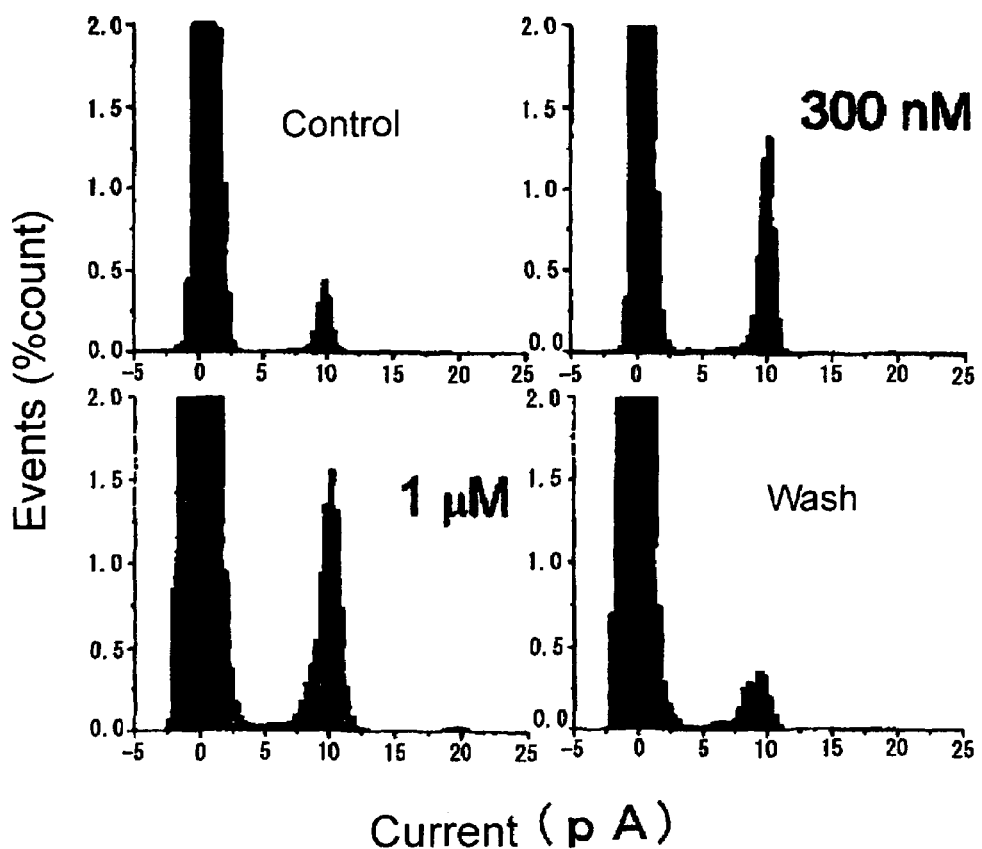
Figure 5C:
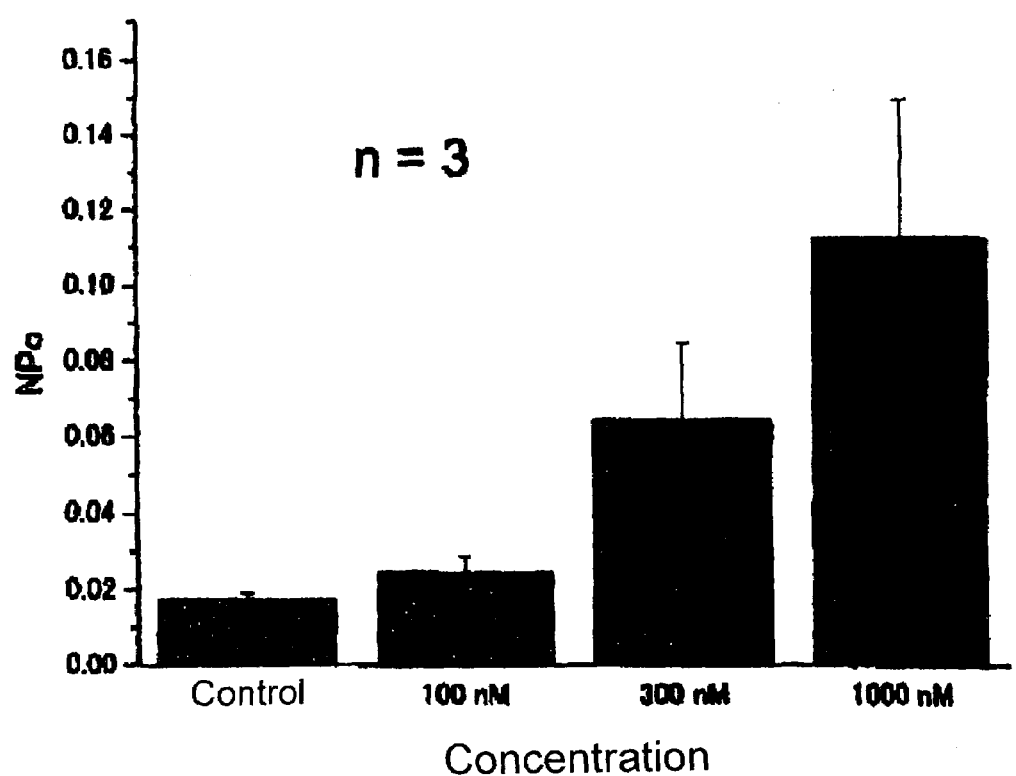

BK channels are activated by increase in the intercellular $Ca^{2+}$ concentration. Therefore, if the test compound has an effect of increasing the intracellular $Ca^{2+}$ concentration, the channel activation may be caused thereby. In this connection, on the whole-cell recordings, 5 mM EGTA and $CaCl_2$ were added into the pipette solution to buffer the intercellular $Ca^{2+}$ concentration to proximity of pCa 6.5, thereby excluding most of the influences channel current recording was carried out. The single channel current was recorded with respect to the cells in which BK(α+β1) channels were constantly expressed, by the inside-out patch clamp technique. The intracellular fluid (the fluid contacting the inner side of the cell membrane) was fixed at pCa 7.0. Holding potential was maintained at +40 mV, and a change in channel opening probability was observed. When the test compound was applied to the inner side of the cell membrane, channel activation was observed at concentration of 100 nM or more, and the effect was removed by washout (FIG. 5A). From the original traces, histograms of the opening and closing events were prepared. Accompanied by application of the test compounds, the peak of approximately 10 pA increased, which shows an opening of the channel, and this effect was removed by washout (FIG. 5B). From these histograms, channel opening probability was calculated to show relation between the concentration and effect as shown in FIG. 5C. From this result, it was shown that the effect of the test compound was concentration-dependent.

Example 3

(Method and Results)

Effects of test compounds on BK channel currents were examined in single HEK293 cell expressing BK(α+β1) channels (hereinafter referred to as HEKBKαβ1) under whole-cell voltage clamp. The $Ca^{2+}$ concentration in the pipette solution was fixed at pCa 6.5 using a $Ca^{2+}$-EGTA buffer. Depolarization from −60 mV to +30 mV induced outward currents in both native HEK293 and HEKBKαβ1, but the current density was much higher in the latter (the current density at the peak: 11.0±1.8 and 95.2±20.9 pA/pF, n=5 and 6, respectively, p<0.05). Application of pimaric acid in a concentration range of 1 to 10 μM increased outward currents in a dose-dependent fashion in HEKBKαβ1 (FIG. 6A), but did not change in native HEK293 (data not shown). This enhancement of outward current by pimaric acid could be removed completely by washout. Effects of other test compounds were also examined in this manner. The peak amplitude of outward current at +40 mV in the presence of 1, 3, and 10 μM resin acids was measured relative to the value taken just before the application (FIG. 6B). Pimaric Acid, sandaracopimaric acid, isopimaric acid, dihydroisopimaric acid, and dihydroisopimarinol showed significant potentiating effects on outward current at concentration of 1 μM and higher (n=4–5, p<0.05 versus 1.0).

To determine whether pimaric acid changes the binding of charybdotoxin (ChTX) to BK channels, the concentration-dependent block of macroscopic currents by ChTX was measured in HEKBKαβ1, in the absence and presence of 10 μM pimaric acid (FIG. 7). The outward currents elicited by depolarization from −60 mV in 10 mV steps were enhanced at potentials positive to −20 mV. The current at +40 mV was increased from 1214±153 to 2527±448 pA (n=5, p<0.05). The addition of 100 nM ChTX significantly reduced the outward current to levels lower than those under the control conditions (FIG. 7, A and B). The remaining components in the presence of 100 nM ChTX include native delayed rectifier $K^+$ currents and unblocked BKαβ1. The currents at +40 mV in the presence of 10 μM pimaric acid was reduced from 2527±448 pA to 499±90 pA (p<0.01 versus before the application of and in the presence of 10 μM pimaric acid). Cumulative addition of ChTX in the range of 3 to 100 nM reduced outward current in a concentration dependent manner (FIG. 7C). A concentration-response relationship for ChTX-induced block was also obtained in the absence of pimaric acid; the current amplitude at +40 mV was reduced from 1233±226 to 205±46 pA by addition of 100 nM ChTX (n=5, p<0.01). The normalized data were well fitted with the Hill equation modified for the concentration-response relationship. $I_{block} = (1-C)/\{1+(K_d/[ChTX])^{nH}\}$, where $K_d$ is the apparent dissociation constant of ChTX, [ChTX] is the concentration of ChTX, $n_H$ is the Hill coefficient, and C is the constant. The $K_d$ obtained from the best fitting were 7.66±2.66 and 6.72±2.26 nM (n=5, p>0.05), in the absence and presence of pimaric acid, respectively. The $n_H$ value, 0.847±0.034 and 0.982±0.161 (p>0.05), respectively, suggest one-to-one binding of ChTX to BKαβ1. The C values which may correspond to the native $K^+$ currents insensitive to ChTX, were 0.077±0.0226 and 0.0965 ±0.0388 (p>0.05), respectively. The data in FIG. 7D show that the relationship in the presence of 10 μM pimaric acid was almost identical with that in its absence. The half-maximum concentrations of ChTX for the block of BK channel current were almost identical each other in the absence and presence of pimaric acid (7.66 and 6.72 nM). These results suggest that pimaric acid does not affect the binding of ChTX to BK channels.

INDUSTRIAL APPLICABILITY

Since the medicament of the present invention has an excellent potassium channel opening effect, and further its effect is specific, it is useful for prevention and/or treatment of essential hypertension, tonic bladder, airway hyperresponsiveness, or ischemic central nervous system disorder.

The invention claimed is:

1. A method of treatment of hypertension, tonic bladder, disturbances of peripheral circulation, airway hyperresponsiveness, sensory neuron hypersensitivity, central spasm or ischemic central nervous system disorder, which comprises administering a compound, or a physiologically acceptable salt thereof as an active ingredient, wherein the compound is represented by the formula:

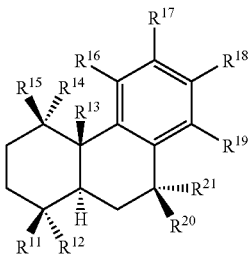

wherein $R^{12}$ is acyl, carboxyl, hydroxamate, sulfo, carbamoyl, sulfonamide or nitrile;

wherein $R^{11}$, $R^{12}$, $R^{13}$, $R^{14}$, $R^{15}$, $R^{16}$, $R^{17}$, $R^{18}$, $R^{19}$, $R^{20}$ and $R^{21}$ are each independently hydrogen, alkyl, alkenyl, halogen, hydroxy, halogenated alkyl, hydroxyalkyl, aminoalkyl, alkoxy, aryl, heteroaryl, acyl, carboxyl, carboxyl, alkoxycarbonyl, hydroxamate, sulfo, carbamoyl, sulfonamide, aldehyde or nitrile; or $R^{20}$ and $R^{21}$ may be bonded to each other to form oxo.

2. The method according to claim 1, wherein $R^{11}$, $R^{13}$, and $R^{18}$ are alkyls, $R^{12}$ is carboxyl, $R^{14}$, $R^{15}$ and $R^{16}$ are hydrogen, or a physiologically acceptable salt thereof.

3. The method according to claim 1, wherein $R^{11}$, $R^{13}$ and $R^{18}$ are alkyls, $R^{12}$ is carboxyl, $R^{14}$, $R^{15}$, $R^{16}$, $R^{20}$, and $R^{21}$ are hydrogen, and $R^{17}$ and $R^{19}$ are halogen, or a physiologically acceptable salt thereof.

4. The method according to claim 1, which method is for treatment of essential hypertension, tonic bladder, airway hyperresponsiveness, or ischemic central nervous system disorder.

5. The method according to claim 1, wherein said compound is dichlorodehydroabietic acid.

* * * * *